United States Patent [19]
Saur et al.

[11] Patent Number: 4,710,472
[45] Date of Patent: Dec. 1, 1987

[54] MAGNETIC SEPARATION DEVICE

[75] Inventors: Joseph W. Saur; Charles P. Reynolds, both of Rockville, Md.; Alfred T. Black, Fairfax, Va.

[73] Assignee: The United States of America as represented by the Secretary of the Navy, Washington, D.C.

[21] Appl. No.: 780,123

[22] Filed: Sep. 25, 1985

[51] Int. Cl.$^4$ ............................................... C12M 1/00
[52] U.S. Cl. .................................... 435/287; 210/222; 209/215
[58] Field of Search ......................... 210/222, 223, 927; 422/44; 209/215, 213, 223.1; 269/8, 276, 246; 435/287

[56] References Cited

U.S. PATENT DOCUMENTS

| | | | |
|---|---|---|---|
| 455,414 | 7/1891 | Searle | 269/246 |
| 775,659 | 11/1904 | Jorgensen | 269/246 X |
| 2,676,504 | 4/1954 | Brugge et al. | 269/8 |
| 3,402,820 | 9/1968 | Lohmann | 210/222 |
| 3,970,518 | 7/1976 | Giaever . | |
| 4,018,886 | 4/1977 | Giaever | 210/222 |
| 4,210,535 | 7/1980 | Risk | 210/222 |
| 4,219,411 | 8/1980 | Yen et al. | 209/213 |
| 4,230,685 | 10/1980 | Senyei et al. . | |

FOREIGN PATENT DOCUMENTS

| | | | |
|---|---|---|---|
| 0136126 | 4/1985 | European Pat. Off. . | |
| 135972 | 11/1902 | Fed. Rep. of Germany | 269/246 |
| 2413816 | 10/1975 | Fed. Rep. of Germany | 269/8 |
| 56744 | 4/1983 | Japan | 269/8 |
| 2144062 | 2/1985 | United Kingdom | 269/276 |
| 617309 | 7/1978 | U.S.S.R. | 269/8 |

OTHER PUBLICATIONS

T4 Technical Bulletin, Clinical Evaluations–Magic TM T4 (Corning Trademark)"Results of Independent Evaluations of Corning's New Magnetic Particle T4 Assay" by Kathleen L. Provost.

Technical Bulletin (Corning), "Magnetisable Particles in Immunochemistry," by Professor John Landon, Dept. of Chemical Pathology, St. Bartholomew's Hospital, London, England.

Transplantation Proceedings, vol. XVII, No. 1 Feb. 1985, "An Immunomagnetic Flow System for Selective Depletion of Cell Populations from Marrow," by C. P. Reynolds, A. T. Black, J. W. Saur, R. C. Seeger, J. Ugelstad and J. N. Woody.

*Primary Examiner*—Samuel Scott
*Assistant Examiner*—H. A. Odar
*Attorney, Agent, or Firm*—John L. Forrest; Wendell R. Guffey; Andrew M. Lesniak

[57] ABSTRACT

A magnetic separation device suitable for removing magnetic bead-coated cells from a system comprising a base, a plurality of magnets mounted on the base such that a sample chamber is created for holding sample containers which are to be placed in close proximity to the magnets, and a means for adjusting the position of the magnets with respect to the sample container. A blood sample containing magnetic bead-coated cells is passed through tubing which is mounted in close proximity to the magnets. The magnetic bead-coated cells are attracted by the magnets and retained in the tubing while the nonmagnetic cells pass through the tubing.

21 Claims, 7 Drawing Figures

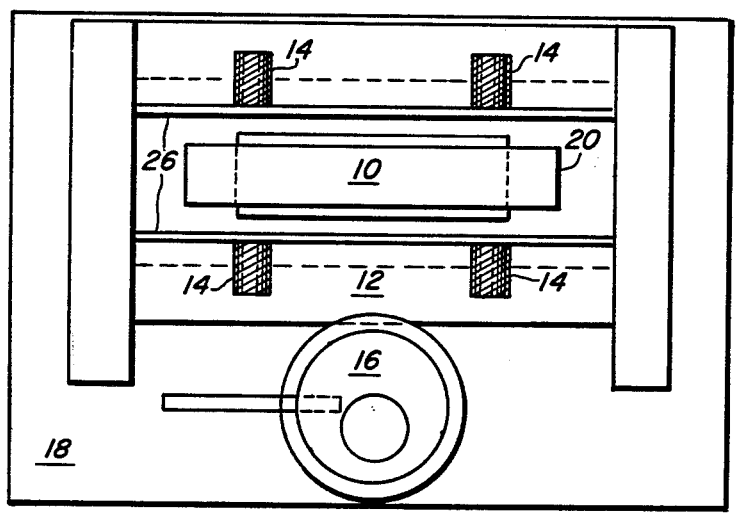 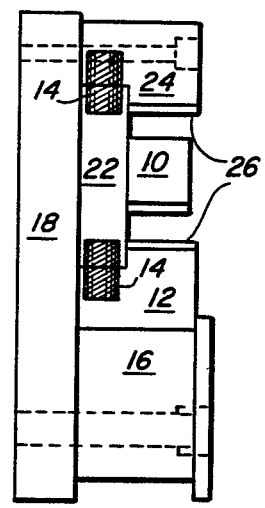
FIG. 1(a)   FIG. 1(b)
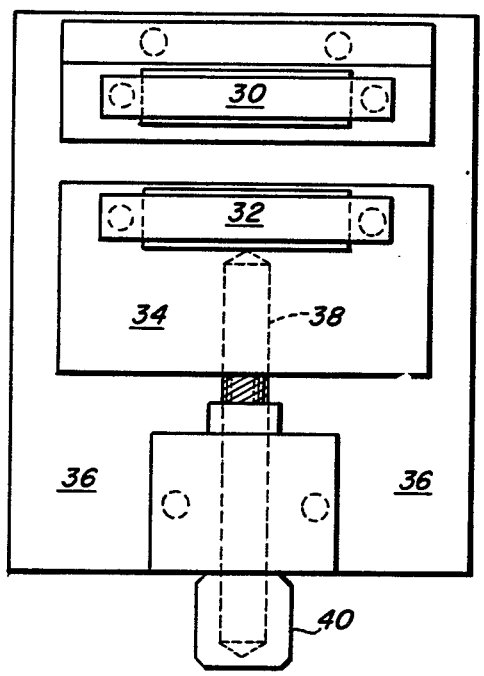 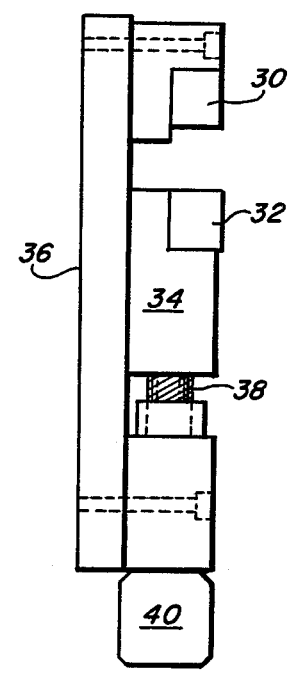
FIG. 2(a)   FIG. 2(b)

MAGNETIC SEPARATION DEVICE

BACKGROUND OF THE INVENTION

This invention pertains to magnetic separation devices and more particularly to magnetic separation devices used to selectively remove magnetic bead-coated cells from tissues such as bone marrow or blood.

Depletion of cell populations from bone marrow has been mainly approached using antibodies conjugated to toxins such as ricin or with antibodies and complement to effect lysis of the target cells. These techniques have several disadvantages including difficulty in measuring the selective cell kill in the marrow, non-specific toxicity of either toxins or complement, and the necessity to prepare large amounts of complement. In addition, many antibodies are neither cytotoxic with complement nor toxin conjugates.

Polymeric microspheres conjugated to antibodies have been used to probe the cell surface for receptor sites using scanning electron microscopy. Molday et al., 64 *J. Cell Biol.* 75–88 (1975). Iron-containing polymeric microspheres tagged with fluorescent dyes conjugated to antibodies were used to separate red blood cells and lymphoid cells by binding the antibody-microsphere to selected cells and exposing the cell population to a magnetic field. Over 99% of the bound cells were attracted by the magnet. Molday et al., *Application of Magnetic Microspheres in Labelling and Separation of Cells*, Nature 268:437-8 (1977). Treleaven et al., *Removal of Neuroblastoma Cells from Bone Marrow with Monoclonal Antibodies Conjugated to Magnetic Microspheres*, Lancet 1:70–3 (1984), used monoclonal antibodies bound to magnetite containing polystyrene microspheres to separate tumor cells from bone marrow. U.S. Patent No. 4,230,685 to Senyel et al. discloses a magnetically responsive microsphere having Protein A on the outer surface. U.S. Pat. No. 3,970,518 to Giaever discloses small magnetic particles coated with an antibody layer that are used to provide large and widely-distributed surface area for sorting out and separating select viruses, bacteria and other cells from multi-cell, bacteria or virus populations. U.S. Pat. No. 4,018,886 to Giaever discloses small magnetic particles that are used to provide large and widely-distributed surface area for separating a select protein from a solution to enable detection thereof when present in low concentrations. The particles are coated with a protein that will interact specifically with the selected protein.

Recently, magnetic microspheres have been attached to target cells using monoclonal antibodies and selectively depleted from bone marrow with high energy magnets in a flow system using magnetic chambers. The technique is promising and has the advantage that physical cell removal is easier to assay than selective cell death in a mixed population. However, difficulty has been encountered in use of the original design magnetic chambers, because of the necessity to clean and sterilize the chambers between patients.

The chambers also provide only a single magnetic surface for each chamber, not providing optimal use of the expensive high-energy magnets. Thus, a device in which a disposable container contacts the marrow being depleted is an advantage. Another improvement needed is a device which allows use of more than 1 side of the magnet. Finally, a device is needed in which a directed high-energy field is concentrated on the cells passing through the flow system, to ensure removal of cells having a small magnetic moment due to attachment of a single bead, or single unattached beads. In the currently employed flow system, a very expensive electromagnet is used for the latter purpose.

SUMMARY OF THE INVENTION

It is, therefore, an object of the present invention to provide a magnetic separation device which can quickly and easily separate magnetic bead-coated cells from nonmagnetic bead-coated cells without cleaning and sterilizing the device between samples.

It is another object of the present invention to produce a magnetic separation device which separates cells without having the magnets contact the sample solution.

It is another object of the present invention to produce a magnetic separation device which is portable and requires no power source.

It is another object of the present invention to produce a magnetic separation device which makes optimal use of high energy magnets.

It is another object of the present invention to produce a magnetic separation device which concentrates the magnetic field on the cells passing through the device.

It is another object of the present device to provide a magnetic separation device for small scale cell sorting (such as in preparing cells for biological or diagnostic tests) that allows rapid, sterile cell sorting.

It is another object of the present device to provide a large scale separation device for sterile separation of human bone marrow harvested for transplantation (to purge tumor cells or alloreactive cells).

These and other objects are achieved by constructing small-portable devices using high energy samarium cobalt magnets which can be adjusted to produce a high strength magnetic field in the sample container. The sample chamber is designed to accept flexible tubing which can be brought in close proximity to the magnets without the necessity that the sample actually contact the device or the magnets. This avoids the requirement that the sample chamber be cleaned and sterilized between samples.

In the preferred embodiment, the magnetic separation device is constructed by mounting two samarium cobalt magnets on acetal plastic blocks which are anchored to an an acrylic base. The magnets are mounted along parallel lines such that a sample chamber for holding sample containers is created between the magnets. One of the magnets is immovably mounted on the acrylic base while the second magnet is mounted such that it can be moved perpendicularly to the parallel lines so as to adjust the position of the second magnet with respect to the sample container and first magnet.

Other objects, advantages, and novel features of the present invention will become apparent from the following detailed description of the invention.

DESCRIPTION OF THE DRAWINGS

FIG. 1(*a*) is an overhead view illustrating a single magnet device which permits tubing to be clamped on both sides of the magnet.

FIG. 1(*b*) is a side view illustrating a single magnet device which permits tubing to be clamped on both sides of the magnet.

FIG. 2(a) is an overhead view illustrating a two magnet device which permits tubing or test tubes to be clamped between the magnets.

FIG. 2(b) is a side view illustrating a two magnet device which permits tubing or test tubes to be clamped between the magnets.

DETAILED DESCRIPTION OF THE INVENTION

Figure 3:
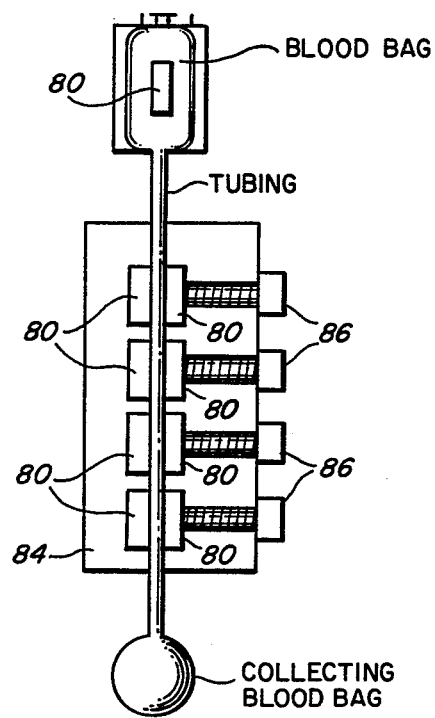
FIG. 3 is a frontal view illustrating multiple magnet device which permits tubing to be clamped between the magnets.

The magnetic separation device of the present invention is constructed by mounting magnets on a base such that a sample chamber is produced which can accommodate a sample container. The magnets are mounted so that the position of the sample container can be adjusted with respect to the position of the magnets to insure very close contact with the sample container. This is desirable because the sample container which holds the sample containing the magnetic bead-coated cells can be adjusted with respect to the magnets to insure that the maximum magnetic field will reach the magnetic beads. By using sample tubes or flexible tubing, the necessity for cleaning and sterilizing the sample chamber between samples is eliminated. The sample never contacts the magnetic separation device, particularly the magnets. The magnetic bead-coated cells are held in place by the magnet while the cells without beads attached are removed from the sample using a pipet or, in the case of the flexible tubing, simply pass through the tubing.

Any material can be used for the base such as wood, metal, or plastic, with plastic being preferred, acetal and acylic plastic being most preferred. Magnetic metals, however, are least preferred since they may interfere with the magnetic fields of the mounted magnets.

Any magnetic substance can be mounted on the base to produce a magnetic field that effects the sample. Iron, steel, and alloys such as cobalt-iron, nickel-iron, aluminum-iron, nicket-zinc and samarium-cobalt are preferred with samarium-cobalt being most preferred. Electro-magnets could also be used but are not preferred because their large size, lack of portability, heat generation, and requirements for a power source.

The magnets can be mounted using any suitable means including glue, brackets, screws, bolts and the such. Either one or all of the magnets are mounted on the base so that the position of the magnets can be adjusted to accomodate the sample container in a sample chamber created by the placement of the magnets on the base. Any means can be used to adjust the position of the magnets on the base but cams and adjusting screws are most preferred.

The sample container can have any size or shape consistent with the size and shape of the base and magnets, with disposable, roundbottom polystyrene or polyethylene test tubes and flexible tubing being the preferred sample containers.

FIG. 1(a) and 1(b) illustrate one embodiment of the magnetic separation device. The device is constructed on a plastic base 18 with a 15×58 mm samarium cobalt magnet 10 anchored to a self-centering delrin base 22 by an aluminum bracket 20. A pair of acetal plastic jaws 12 24 which have optional galvanized steel shims 26 mounted on the jaws are closed by a delrin cam 16. Strong beryllium copper springs 14 in the base of the clamp facilitate separation of the jaws and magnet when inserting the tubing and insure that the base 22 is positioned such that the magnet is centered between the two sample containers. The jaws allow clamping 1 cm diameter tubing between the magnet and the galvanized steel shims on both sides of the magnet. The metal shims on the clamp generate a magnetic field induced by the magnet. Thus, cells flowing through tubing clamped in the device are exposed to four 15×58 mm magnetic surfaces generated by a single magnet. The flow chambers in the magnetic field are formed by flattening the tubing such that cells flow through a 1.5 mm-thick chamber, with a maximum distance of 2.25 mm from a magnetic field at any time in the chamber. The device clamps the tubing to form two chambers per device.

The ability to form chambers by clamping tubing in the device provides for rapid disposal of the tubing used, facilitating use of the device in a clinical situation. Cleaning and sterilizing the older depletion chambers has been a major problem during clinical application of marrow depletion. The clamp system allows use of readily available presterilized, disposable, non-pyrogenic tubing for the portion of the device actually contacting the patient's cells. This provides a more secure sterile environment and avoids difficulties associated with the cleaning and sterilizing of chambers. Being able to unclamp and remove the tubing also permits rapid removal of the bead-coated cells from the magnetic surface. This allows the cells depleted by the magnets to be quickly harvested. Clamping the tubing on both sides of the magnet coupled with the addition of magnetizable strips on sides opposite from the magnet provides four magnetic surfaces per device. The additional magnetic surfaces provide more efficient removal of cells with beads attached and make better use of the costly high-energy samarium cobalt magnets.

FIG. 2(a) and 2(b) illustrate another embodiment which employs two 15×58 mm samarium cobalt magnets 30 32 mounted along parallel lines on acetal plastic blocks which are anchored to an acrylic base 36. An adjusting screw 38 allows the magnets to be moved closer together or farther apart. Magnet 30 is immovably mounted on the base and magnet 32 is mounted on a moveable block so that it can be moved with respect to magnet 30 by adjusting screw 38 using knob 40. Thus, test tubes, centrifuge tubes, flexible tubing and other sample containers can be clamped firmly between the two magnets. The two magnets are oriented with opposite poles across from one another (i.e., north across from south). The opposition of the two samarium cobalt magnets generates a very high energy magnetic field in the sample containers clamped in the device. For rapid cell separation in tubes, the tube containing cells and beads is clamped in the device, and the device placed so that the tube is vertical, with the bottom of the tube below the magnets. Cells with magnetic beads are attached to the sides of the tube in a few seconds due to the strong magnetic fields. The user can then insert a Pasteur pipet into the tube and withdraw the cells without beads attached from the bottom of the tube. This can be done quickly and easily without disturbing the bead-coated cells on the side of the tube. Harvest of bead attached cells can then be easily accomplished by adding medium to the tube and removing the tube from the depletion device. The bead-coated cells will then go into suspension in the tube.

The double magnet device provides a previously unavailable rapid cell separation device for small-scale separations for magnetized cells. The high strength of the magnetic field due to the opposing magnets used in this device allows very rapid and efficient separation of the cells. The high-energy field generated by the two magnets in opposition is also useful in flow through depletion devices, in which tubing is clamped in the device. Using the two devices together has completely removed any beadcoated cells or free beads, without the need for the expensive electromagnet described in the original magnetic depletion system. This provides a more portable and less expensive system.

FIG. 3 illustrates large scale magnetic sorting device in which three or four pairs of magnets 80 are mounted on an acetal plastic block 82 which is in turn mounted on an acrylic base 84. The size of the sample chamber holding the tubing is also adjusted by screws 86. The magnets are mounted so that the solution flow passes through three or four separate magnetic fields in series. Obviously the more magnet sets used the greater the efficiency of the device.

Figure 4A:
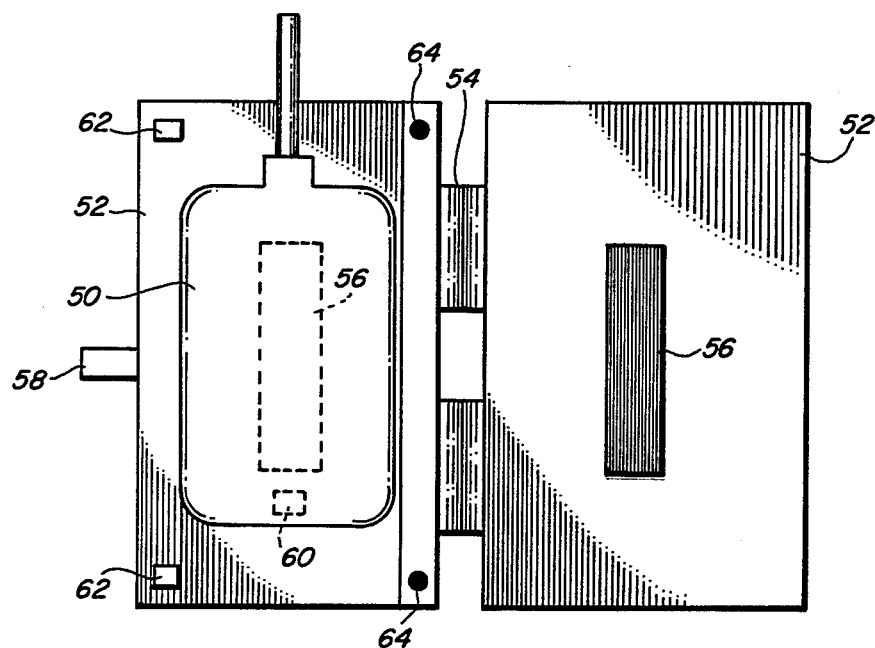
FIG. 4(a) is an overhead view illustrating a two magnet device which permits blood bags to be clamped between the magnets on a base which can be rotated to attach bead-coated cells to the side of the bag, and then suspend the cells so that unattached cells flow into another bag. Tubing from the bag-magnet device can be routed through the multiple magnet device (FIG. 3) to insure removal of all bead-coated cells and free beads.
Figure 4B:
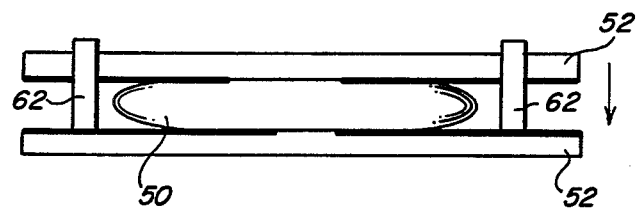
FIG. 4 (b) is a side view illustrating the two magnet device shown in FIG. 4(a).

FIG. 4(a) and 4(b) illustrate another embodiment of the magnetic separation device which can be used for large scale separations. The marrow with immunomagnetic beads is contained in sterile, disposable transfer packs or blood bags 50. The bags 50 may be any size but 150 ml, 300 ml or 600 ml bags are preferred, depending on the size of the device used. The transfer pack 50 is placed in the "book like" depletion device and held there by a mounting peg 60. The device has two base plates 52. One base plate rotates about hinges 54 to close the plates on the transfer pack 50. The base plate with the hinges is attached to the bottom base plate by posts 64 which allow the two base plates to move closer to one another while remaining parallel to one another and to the sides of the transfer pack. Thus, as the cells are drained from the transfer pack, the base plates move closer together, avoiding any free space between magnets and the sides of the transfer pack. Each base plate 52 has a magnet 56 mounted in about the center of the plate. The device is latched closed with the spring latch 58. The bag and device are mounted on a wheel using posts 62 and rotated for about 15 minutes. The majority of the beads and cells with beads then attach to the sides of transfer pack or blood bag near the magnets.

Following this, the device and transfer pack are removed from the wheel and hung over a tubing depletion device, preferably the device shown in FIG. 3 in which four pairs of magnets are used to compress the outlet tubing from the bag. The marrow is run through the tubing, past the magnets which retain any beads and bead-coated cells on the side of the tubing, and into another transfer pack.

The devices disclosed here are employed in a clinical size bone marrow separation flow-through system for depletion of tumor cells, T cells, or other specific cell types from marrow harvested for transplantation. The two magnet device is used for rapid, small-scale separations of cells in the laboratory and also in the clinical flow depletion system. The one magnet device or a series of two magnet devices can be used for large scale and clinical applications. Either device can separate cells which have magnetic particles bound to the outer membrane.

A variety of metallic particles which are attracted by a magnet can be used. Examples include carbonyl iron for monocyte depletion, iron-impregnated plastic microspheres with absorbed goat anti-mouse antiserum which will attach to target cells coated with mouse monoclonal antibodies, iron-impregnated dextran beads attached to antibodies, or iron-impregnated bovine serum albumin beads attached to staph protein A.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Polystyrene magnetic beads were prepared from styrenedivinyl benzene polymer, 3 microns in diameter, magnetite content corresponding to 27.4% by weight of iron. Affinity purified goat anti-mouse immunoglobulin GAM at a concentration of 200 mcg/mg of beads, was incubated with the beads (1 mg/ml) in 0.1M phosphate buffer, pH 7.4 on a rotating wheel at 22° C. for 18 hours. Unbound GAM was removed by washing. Normal human bone marrow was obtained from vertebral bodies and used fresh, or occasionally cryopreserved and thawed before use. The viable mononuclear cells were separated by density centrifgation with Ficoll-Hypaque. Neuroblastoma cells, which had been marked with the supravital DNA stain Hoechst 33342 (H342), were seeded into the marrow mononuclear cells. Neuroblastoma cells seeded into marrow included single cells and small to moderate sized clumps, thus accurately simulating metastatic neuroblastoma in the marrow. The premarking of the tumor cells with H342 allowed accurate quantitation of the number of tumor cells in the marrow, before and after immunodepletion. The fluorescence of the H342 labeled cells is sufficiently bright to allow detection of one marked tumor cell per million marrow cells. Counterstaining the tumor/marrow mixture with the vital dye trypan blue limits the detection of tumor cells to only viable cells, as trypan blue quenches the nuclear H342 fluorescence in non-viable cells. Quantitation of tumor cells in marrow from patients was done by immunoperoxidase staining using rabbit antiserum to neuron specific enolase and monoclonal antibodies to cell surface antigens. This method accurately detects one tumor cell per 50,000 marrow cells.

For purging experiments, 50 or 100 million bone marrow cells were seeded with 10 to 20% H342 stained neuroblastoma cells. The cell mixture was incubated in monoclonal antibodies for 1 hr at 4° C., washed twice in RPMI 1640+10% fetal calf serum, and mixed with GAM-coated beads (100 per tumor cell) for 1 hour at 4°C., on a rotating wheel. The sample was then diluted 3-fold, and passed over 15×48 mm samarium cobalt magnets to retain free beads and bead-coated cells. Quantitation of myeloid stem cells (CFU G,M) was done after 10 days growth in agar with leukocyte conditioned medium. Target cells are first coated with antibodies which do not bind to hematopoietic stem cells.

After washing to remove excess antibody, magnetic beads that have goat anti-mouse Ig attached (GAM) are incubated with the marrow. The beads attach to the antibody-coated target cells, allowing selective removal of the cells with high energy magnets.

For these model experiments, 3 different magnetic devices were tested. In one set of experiments marrow ($50-100 \times 10^6$ cells) with H342-marked neuroblastoma cells, stained with antibodies and then magnetic beads, was placed in a 50 cc syringe and allowed to flow slowly (5 mls/minute) through tubing clamped in 2 identical devices such as shown in FIG. 1, thus providing 8 magnetic surfaces to attach beads and bead-coated cells. In a second set of experiments, $50-100 \times 10^6$ marrow cells were seeded with H342 marked neuroblostoma cells, incubated with monoclonal antibodes to neuroblastoma, washed and then incubated with GAM-coated beads. The marrow-tumor bead mixture was then placed in a 15 ml round bottom polystyrene centrifuge tube and clamped in the 2 magnet device shown in FIG. 2. After rocking the device for approximately one minute to move the fluid, cells, and beads over the magnets, the tube cap was removed and the unattached cells withdrawn with a pasteur pipet.

Consistent depletion of 3 to 4 bags of neuroblastoma cells have been obtained using both of the above procedures with the two different devices. However, the yield of recovered marrow cells is always higher using the second procedure described above, because of non-specific losses of cells trapped in loops of tubing formed by the device in FIG. 1. For that reason, a device was constructed for large scale clinical applications (described below) which maintains the tubing perpendicular to the deck and straight, with no loops, avoiding trapping of cells.

In addition to depletion of neuroblastoma cells from marrow, the second procedure described above has been used with marrow seeded with H342-marked T cell leukemia cells and consistent 4 to 4.8 log depletions of T-leukemia cells performed (using the device shown in FIG. 2).

After purging, no neuroblastoma cells were detectable by immunoperoxidase staining for neuron specific enolase and cell surface monoclonal antibodies (sensitivity 1/50,000). The recovery of total cells in the marrow was 58%, with no reduction in the number of CFU G,M.

EXAMPLE II

Bone marrow removed from a neuroblastoma patient was incubated with an antibody cocktail consisting of (HSAN 1.2, RB 21-7, Ab390, Ab459, and BA-1). Following the incubation, the tubes were centrifuged, the antibody containing medium was aspirated down to a dry pellet, and the cells resuspended again in 250 mls of medium plus FCS and recentrifuged. After the second centrifugation, the cells were resuspended in fresh medium plus FCS at a concentration of 25–30 million cells per ml.

150 ml transfer bags were then fitted with a blood administration set. The air vent of the blood administration set was fitted with a 50 ml syringe to use as a port to introduce the cells and beads into the bag. The cell suspension was pipetted into the 50 ml syringe. Enough cells and medium were added so that the 150 ml volume of the bag was complete and the concentration of the cells was 20 million per ml. When the majority of the cells have entered the bag, the appropriate quantity of goat anti-mouse Ig (GAM)-coated magnetic beads for the 150 mls of cells at 20 million cells per ml is added. The number of GAM-coated beads was determined by the following formula: (% target cells/100)×(total number of cells)×100. If no tumor cells were known to be in the marrow at time of harvest, 0.5 percent can be used.

Following this, fresh medium with FCS was added to the barrel of syringe so that the total volume in the bag was 150 ml. The latter was flushed into the syringe by placing the plunger of the syringe back into the barrel while pressing down a few centimeters. When the medium had entered the bag, the syringe was removed from the vent port and the injection site used to tightly cap the vent port.

Bags containing the cells and the magnetic beads were then placed in the cold room on a rotating wheel for a 30 minute incubation at room temperature. After the 30 minute incubation, the bag was placed into the magnetic depletion device which was attached to a rotating wheel. The magnetic depletion device was quickly locked into place and rotated on the wheel for 15-minutes. After rotation of the magnetic depletion device on the wheel, the device and bag are removed from the rotating wheel and hung on the laminar flow hood over the 8 magnet magnetic depletion device (FIG. 3). The tubing fits into this device. The depletion device was oriented outside the laminar flow hood so that the cell suspension can be collected into 250 ml centrifuge tubes in the hood. Flow rate through the magnetic depletion device was maintained at 5 to 10 mls per minute. In other cases, the device was set up so that the marrow flowed from the bag magnetic device, through the 8 magnet tube device, and into another blood bag or transfer pack. This provides a sterile closed system and avoids the necessity of setting up the devices outside a laminar flow hood.

After all of the cell mixture had flowed out of the bags, the injection site covering the vent on the blood administration port was cleansed with betadine and then with a sterile alcohol prep pad, and 20–30 mls of fresh medium with FCS was injected through the injection site into the bag to flush out remaining cells in the bag. Care was taken not to introduce too much of the flush at any one time. This avoided the flush volume rising to the level where the magnetic beads were trapped against the magnet and dislodging cells or beads. The flush is collected as described for the cells in the tube.

After purging the first time, a cell count is obtained. Unless the cell count was low enough to prevent it, the antibody incubation and bead depletion steps above are repeated for a second cycle. Cells were incubated in the same concentration of antibody in 250 ml tubes at $1-2 \times 10^7$/ml. Bead/target cell ratio was calculated based on the starting tumor concentration, but the total cell number remaining after the first purge was used.

The magnetic depletion devices are used to selectively remove cells from tissues such as blood or bone marrow containing a mixture of any cell types. The devices can be used to deplete a cell population from the tissue. Another use is to selectively concentrate a cell population in blood, marrow, or a suspension of cells from lymph nodes or spleen, to aid in detection, or in order to purify the cell sub-population. Selective depletion or enrichment of cell types with the device is accomplished using various types of immunomagnetic microspheres which selectively attach to target cells, or other objects coated with specific monoclonal antibodies. Utility may also be seen in concentrating or removing substances from a mixture.

Another application of cell separation technology is in preparing cell suspensions for various biological assays. In such cell separation procedures, subpopulations of interest to the assay are concentrated by positive selection or by selective removal of unwanted cells. Currently, such concentration methods employ lengthy and fairly inefficient separation methods. The magnetic bead technique which provides a possible solution for the delays and inefficiency of bead-coated cells, has previously been unavailable. Such a device should allow rapid and efficient cell separation for various biological studies.

An example of concentrating cells using the device in FIG. 2 is as follows. Bone marrow containing 10% neuroblastoma cells is incubated with anti-hemotopoietic antibodies W6/32, L227, BBM.1, and GAP 8.3 (which do not bind to neuroblostoma) for 10 minutes, washed and then incubated with 2 GAM-coated magnetic beads per marrow cell for 10 minutes on a rotating wheel in a 15 ml round bottom centrifuge tube. The tube with marrow and beads is then clamped in the 2-magnet device, and after attachment of beads and bead-coated cells, the unattached cells removed. The unattached cells were enriched for tumor (7 to 10 fold enrichment). Yield and purity of the enriched tumor from marrow has allowed measurement of the number of copies of the N-myc gene, on important prognostic test for for neuroblostoma patients.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A magnetic separation device suitable for removing magnetic bead-coated cells from a system, comprising:
   at least one sample container containing a sample of magnetic bead-coated cells;
   a base;
   magnetic means comprised of at least one high energy magnet mounted on said base such that at least one chamber is created near said high energy magnet for holding at least one sample container on said base near said high energy magnet, and a sample container placed in said chamber in close proximity to said magnetic means so that magnetic bead-coated cells within said sample container are attracted by said magnet during use of said device; and
   means for adjusting the position of at least one said high energy magnet with respect to said sample container in said chamber.

2. A magnetic separation device suitable for removing magnetic bead-coated cells from a system, comprising:
   a base; and
   a high energy magnet mounted on said base such that two chambers are created on opposite sides of said high energy magnet for holding two sample containers which are to be placed in said chambers in close proximity to said high energy magnet.

3. A magnetic separation device for removing magnetic bead-coated cells from a system comprising:
   a base;
   a plurality of high energy magnets mounted on said base such that a chamber is created for holding a sample container which may be placed into said chamber in close proximity to said magnets which are located at opposite sides of said chamber;
   said plurality of high energy magnets having at least two pairs of high energy magnets so that one magnet from each pair is located on one side of said chamber; and
   means for adjusting the position of said one magnet of each pair of magnets with respect to a sample container positioned in said chamber on said base.

4. A magnetic separation device suitable for removing magnetic bead-coated from a system, comprising:
   two base plates;
   means for holding said base plates together such that said base plates can be positioned opposite to each other to create a chamber for holding a sample container;
   a plurality of posts mounted on said base plates which allow said base plates to move closer to each other while remaining in alignment with each other;
   a plurality of mounting pegs mounted on said base plates for holding said sample container in said chamber;
   one or more high energy magnets mounted near the center of each said base plate; and
   means for securing said base plates together so that they will remain secured together while said device is rotated.

5. A magnetic separation device suitable for removing magnetic bead-coated cells from a system, comprising:
   a base;
   a samarium cobalt magnet mounted on said base;
   two jaws mounted on said base on opposite sides of said magnet thereby creating two chambers on opposite sides of said magnet for holding two sample container on said base between said jaws and said magnet, said jaws each being movable with respect to said magnet so as to adjust the position of each said jaws with respect to each said sample container and said magnet; and
   a cam for adjusting the position of said jaws with respect to said sample containers and said magnet.

6. A magnetic separation device for removing magnetic bead-coated cells from a system, comprising:
   a sample container containing a sample of magnetic bead-coated cells;
   a base;
   two blocks mounted on said base, said blocks being mounted in parallel relation on opposite sides of a chamber, the first of said blocks being immovably mounted on said base, the second of said blocks being moveably mounted on said base such that this second blocks can be moved toward or away from the first block;
   respective samarium cobalt magnets, including first and second magnets mounted on said blocks, said respective magnets being mounted along said parallel lines so that a chamber for holding said sample container on said base is created between said first and second magnets, said sample container being mounted in said chamber so that magnetic bead-coated cells within said sample container are attracted by said magnets during use of said device, the first of said magnets being mounted on said block, and the second of said magnets being mounted on said second block such that the second of said magnets can be moved so as to adjust the position of said second of said magnets with respect to said sample container and said first of said magnets; and an adjusting screw mounted adjacent to said second of said magnets and said second of said blocks for adjusting the position of said second of said magnets with respect to said sample container.

7. A magnetic separation device for removing magnetic bead-coated cells from a system, comprising:
a sample container containing a sample of magnetic bead-coated cells;
a base;
a plurality of high energy mounted on said base such that a chamber is created between said high energy magnets for holding said sample container which is disposed within said chamber in close proximity to said magnets so that magnetic bead-coated cells within said sample container are attracted by said magnets during use of said device; and
means for adjusting the position of one of said high energy magnets with respect to said container in said chamber.

8. The magnetic separation device of claim 3, further comprising:
at least two moveable blocks mounted on said base, said blocks being mounted along parallel lines; and
at least two high energy magnets from said plurality of high energy magnets mounted on said moveable blocks, one such magnet mounted on each moveable block from two high energy magnets being mounted along parallel lines such that said chamber is created between them, and two other high energy magnet mounted on said base magnets being mounted on said moveable block such that each can be moved along one of said parallel lines so as to adjust the position of said two high energy magnets with respect to said container.

9. The magnetic separation device of claim 7 having one pair of magnets.

10. The magnetic separation device of claim 9 wherein said means for adjusting the position of one of said high energy magnets with respect to said sample container in said chamber is an adjusting screw.

11. The magnetic separation device of claim 10 wherein each of said high energy magnets is a samarium cobalt magnet.

12. The magnetic separation device of claim 2, further comprising:
two jaws mounted on said base on opposite sides of said high energy magnet thereby creating said two chambers which are useful for holding said two sample containers between said jaws and said high energy magnet so as to adjust the position of each of said jaws with respect to said sample containers and said high energy magnet.

13. The magnetic separation device of claim 12 wherein said jaws each have a magnetically susceptible metal shim which becomes magnetic when in close proximity to said high energy magnet.

14. The magnetic separation device of claim 13 wherein each said shim is made of galvanized steel.

15. The magnetic separation device of claim 14 further comprising:
cam means for adjusting the position of said jaws with respect to said sample containers.

16. The magnetic separation device of claim 15 wherein said magnet is a samarium cobalt magnets.

17. The magnetic separation device of claim 5 wherein each of said jaws has a magnetically susceptible metal shim which becomes magnetic when in close proximity to said magnet.

18. The magnetic separation device of claim 17 wherein each said shim is made of galvanized steel.

19. The magnetic separation device of claim 4 wherein said high energy magnet mounted near the center of each said plate is a samarium cobalt magnet.

20. The magnetic separation device of claim 19 wherein said means for holding said base plates together includes a hinge.

21. The magnetic separation device of claim 20 wherein said means for securing said base plates together includes a spring latch.

* * * * *